United States Patent [19]

Townsend et al.

[11] Patent Number: 5,492,826
[45] Date of Patent: Feb. 20, 1996

[54] APPARATUS AND METHOD FOR SEEDING ENDOTHELIAL CELLS

[75] Inventors: Laurace E. Townsend, Grosse Pointe Park; Michael J. E. Borrelli, Troy, both of Mich.; Diane E. Maupin, Spring Valley, Ohio

[73] Assignee: William Beaumont Hospital, Royal Oak, Mich.

[21] Appl. No.: 165,951

[22] Filed: Dec. 10, 1993

[51] Int. Cl.$^6$ ............................... C12N 5/06; C12M 3/04
[52] U.S. Cl. ........................ 435/240.23; 435/240.241; 435/289.1; 435/298.2; 435/304.1; 600/36; 623/1
[58] Field of Search ..................... 435/1, 240.22, 435/240.23, 240.241, 240.242, 240.243, 283, 284, 285, 286, 312, 296, 310, 316, 809; 600/36; 623/1

[56] References Cited

U.S. PATENT DOCUMENTS

| | | |
|---|---|---|
| 3,883,393 | 5/1975 | Knazek et al. . |
| 4,024,020 | 5/1977 | Weiss et al. . |
| 4,238,568 | 12/1980 | Lynn ........................ 435/285 |
| 4,283,495 | 8/1981 | Lynn ........................ 435/284 |
| 4,495,288 | 1/1985 | Jarvis, Jr. et al. ........... 435/182 |
| 4,647,539 | 3/1987 | Bach ........................ 435/284 |
| 4,824,787 | 4/1989 | Serkes et al. ............... 435/285 |
| 4,845,038 | 7/1989 | Barr et al. .................. 435/296 |
| 4,871,671 | 10/1989 | Errede et al. ............... 435/182 |
| 4,908,013 | 3/1990 | Muller et al. ................ 623/1 |
| 4,912,058 | 3/1990 | Mussi et al. ................ 435/285 |
| 4,962,033 | 10/1990 | Serkes et al. ............... 435/284 |
| 4,988,623 | 1/1991 | Schwarz et al. ............. 435/286 |
| 5,035,708 | 7/1991 | Alchas et al. ................ 623/1 |
| 5,104,802 | 4/1992 | Rhodes et al. ............... 435/311 |
| 5,171,261 | 12/1992 | Noishiki et al. .............. 623/1 |

FOREIGN PATENT DOCUMENTS

| | | |
|---|---|---|
| 59-21388 | 2/1984 | Japan . |
| 2002814 | 2/1979 | United Kingdom . |
| 2094832 | 9/1982 | United Kingdom . |
| 8203764 | 11/1982 | WIPO ....................... 623/1 |

OTHER PUBLICATIONS

Shunya S. et al., "Improved patency of collagen–impregnated grafts after in vitro autogenous endothelial cell seeding" *J. Vas. Surg.* 6(4):325–32 (1987).

van Oene, G. H., et al., "Smooth Muscle Cell Seeding Enhances Neo–Endothelialization" *1st Eur. Workshop Advanced Technologies in Vascular Surgery*, Vienna 1986, pp. 160–166 (Karger, Basel 1987).

Zilla, P. et al., "Endothelial cell seeding of polytetrafluoroethylene vascular grafts in humans: A preliminary report", *J. Vas. Surg.* 6(6):535–41 (1987).

Kaehler, J. et al., "Precoating substrate and surface configuration determine adherence and spreading of seeded endothelial cells on polytetrafluoroethylene grafts", *J. Vas. Surg.*, 9:535–541 (1989).

Zilla, P., et al., "Use of fibrin glue as a substrate for in vitro endothelialization of PTFE vascular grafts",; *J. Surg.*, 105(4):515–522 (1989).

(List continued on next page.)

*Primary Examiner*—William H. Beisner
*Attorney, Agent, or Firm*—Harness, Dickey & Pierce

[57] ABSTRACT

An apparatus and method for culturing living endothelial cells is provided. The apparatus comprises a cell growth container, which in a preferred embodiment is a synthetic graft, heat crimped at both ends. The apparatus further comprises a rotation container that may contain the cell growth container and is attached to a rotation apparatus. The apparatus further comprises fixturing apparatus, which in a preferred embodiment is a pair of o-ring members, that enhances a separated condition of the cell growth container within the rotation container. The method of the present invention comprises providing a culture that includes living cells and a growth medium, introducing the culture into a cell growth container, heat crimping the cell growth container to substantially seal the cell growth container, and positioning fixturing apparatus upon the external surface of the cell growth container. This assembly is inserted into a rotation container, which is rotated by a rotation apparatus.

8 Claims, 1 Drawing Sheet

OTHER PUBLICATIONS

Gerlach, J., et al., "Endothelial Cell Seeding on Different Polyurethanes", *J. Artif. Organs.* 13(2):144–7 (1989).

Gerlach, J., et al., "Endothelial cell seeding on PTFE vascular prostheses using a standardized seeding technique", *Intl. J Artif. Organs* 12(4):270–5 (1989).

Budd, J. S., et al., "Attachment of indium–111 labelled endothelial cells to pretreated polytetrafluoroethylene vascular grafts", *Br. J. Jurg.*, 76:1259–61 (1989).

James, N. L., et al., et al., "Endothelial Cell Seeding of Small Diameter Vascular Grafts", *J. Artif. Organs* 14(5):355–60 (1990).

Thomson, George J. L., et al., "Adult human endothelial cell seeding using expanded polytetrafluoroethylene vascular grafts: A comparison of four substrates" *J. Surg.* 109(1): 20–7 (1991).

Miyata, Etsuro, et al., "Delayed Exposure to Pulsatile Shear Stress Improves Retention of Human Saphenous Vein Endothelial Cells on Seeded ePTFE Grafts", *J. Surg. Research* 50(5):485–93 (1991).

Budd, J. S., et al., "Effects of two methods of endothelial cell seeding on cell retention during blood flow", *Br. J. Surg.* 78:878–882 (1991).

Newman, Kurt D., et al., "Quantification of Vascular Graft Seeding by Use of Computer–Assisted Image Analysis and Genetically Modified Endothelial Cells", *J. Vas. Surg.* 14(2): 140–6 (1991).

APPARATUS AND METHOD FOR SEEDING ENDOTHELIAL CELLS

FIELD OF THE INVENTION

This invention relates generally to cell culture methods and devices, and more particularly to an apparatus and method for seeding endothelial cells on the inside of synthetic graft material.

BACKGROUND OF THE INVENTION

Arterial replacement during surgical procedures has employed the use of prosthetic grafts as an alternative to actual vein replacements. These prosthetic grafts are made from such materials as expanded-polytetrafluoroethylene (ePTFE), polyacrylonitrile polymers, polystyrene, polyester and polyethylene terephthalate. Although the use of synthetic grafts have been successful for the replacement of larger vessels such as the aorta, synthetic graft replacement has often been unsuccessful in the replacement of smaller vessels. The absence of a functional, non-thrombogenic endothelial cell monolayer on the luminal surfaces of small diameter prostheses appears to be a major factor limiting long term patency. Therefore, it is desirable prior to implantation of prosthetic grafts that a seeding of endothelial cells onto the luminal surface takes place.

Because the number of human endothelial cells that can be harvested from the limited lengths of donor vessel available is low, it is desirable to develop methods for enhancing cell attachment and subsequent spreading of these cells. The aim of this type of research is to optimize the formation of a functional, non-thrombogenic endothelial cell monolayer by improving cell attachment onto the inner surface of graft material using various surface coatings. See Budd, J.S., et al., *Br. J. Surg.* 76:1259–1261 (1989). Another related aim of this type of research is to develop methods for introducing various substances and products into the blood system by the seeding of genetically-altered endothelial cells.

Shortcomings associated with replacement vascular grafts have included disappointing graft endothelialization, thus significant luminal thrombus formation resulting in poor long term patency. In addition, the formation of a confluent endothelial cell monolayer on the graft following implantation has been poor, probably due to significant cell losses from the graft surface resulting from the stresses of pulsatile blood flow. Prior studies have indicated that the formation of a firmly attached endothelial monolayer on the inner graft surface before implantation provides a much more stable base for the duplication and spreading of cells following implantation which leads to non-thrombogenicity and permanence of the graft.

Endothelial cell seeding on the inner surface of synthetic grafts has been the focus of research efforts toward producing synthetic grafts which are essentially non-thrombogenic. It has been noted that the use of certain growth media significantly improves the initial attachment of endothelial cells onto synthetic grafts in a static system. See Budd, J.S., et al., *Br. J. Surg.* 78:878–882 (1991).

Known methods for cell seeding on synthetic grafts have included coating the luminal graft surface with an enhancing substance, such as fibronectin, before introducing a cell suspension into the graft. The cell suspension commonly includes endothelial cells that are harvested from human veins by flushing into a first suspension and centrifuging to produce a cell pellet. This cell pellet is resuspended in a growth medium to produce a cell suspension suitable for introduction into the synthetic graft. The synthetic graft containing the cell suspension on its luminal surface is incubated within an incubation chamber for a period of time to allow attachment of endothelial cells to the inner surface of the graft. In this incubation procedure the ends of the graft are sealed to keep the cells and medium inside, and provide a favorable cell growth environment, preventing the evaporation of the cell growth medium from within the synthetic graft. The synthetic graft is also slowly rotated during the incubation period to provide an even distribution of endothelial cells throughout the inner surface of the graft material by evenly distributing the cell suspension.

Known methods for sealing the ends of a synthetic graft have included the use of rubber or plastic plugs or clips, clamps, sutures or glass plugs with a syringe fitting at one or both ends. The use of these external sealing means, however, can be cumbersome and inconvenient, especially when sealing synthetic grafts of small diameters. In addition, these external means for sealing the ends of synthetic grafts can fail to provide graft ends that are completely closed or can become separated from the graft by changes in temperature, pressure or orientation of the graft, as well as by movement of the graft associated with its handling.

Known methods for culturing cells within an incubation chamber have included the insertion of an EPTFE piece inside a glass bottle with TEFLON® tubing attached at each end. The EPTFE piece in this arrangement was taped to the inside surface of the bottle. James et al., *Artif. Organs* 14:355–360 (1990). In another method, a glass tube, itself a substitution for EPTFE, was used as a cell growth chamber with cells growing on the inside surface of the glass tube. This tube was inserted into a rotation device. *Int. J. Artif. Organs* 12(4): 270–5 (1989). Many of the known methods are cumbersome, however, in that they utilize either a large number of tubes within a single roller bottle, or employ a single mechanical rotating device for rotating only a single tube.

The disadvantages associated with these methods have included the failure of the graft to be separated from the interior surface of the surrounding tube or bottle for purposes of maintaining uniform temperature and humidity. Also, when the external diameter of the synthetic graft is substantially smaller than the internal diameter of the glass or plastic tube or bottle surrounding the synthetic graft in the rotation device, the repetitive loss of frictional contact between the external graft surface and the internal test tube surface with rotation of the tube or bottle can result in a repetitive sliding of the synthetic graft within the tube or bottle during rotation by a rotation device. Such movement of the graft within the tube or bottle is undesirable because it can be associated with sudden jarring movements at the point of friction loss and can therefore cause a detachment of endothelial cells from the inner surface of the graft.

The need therefore exists for a method for sealing the ends of a synthetic graft conveniently and substantially, without the need for external sealing means. The need also exists for separating the graft with respect to a rotation container during incubation, such that the synthetic graft rotates smoothly in response to rotation of the rotation device without any slipping or jarring caused by loss of frictional contact between the external graft surface and the internal test tube surface.

SUMMARY OF THE INVENTION

In accordance with the present invention, an improved apparatus and method for culturing endothelial cells is provided. The apparatus includes a hollow cylindrical cell growth container, which in a preferred embodiment is a synthetic graft made from expanded polytetrafluoroethylene or other suitable material. The cell growth container is substantially sealed by heat crimped ends. The apparatus further includes a rotation container for containing the cell growth and rotating it within a rotation device, such as a roller drum. At least one retaining means is positioned upon the external surface of the synthetic graft for enhancing a separated relationship between the cell growth container and the rotation container. In a preferred embodiment, the retaining means includes two o-ring washers positioned upon the external surface of the cell growth container whose outer diameters are smaller than the internal diameter of the rotation container within which the cell growth container is placed.

The method of the present invention comprises the steps of introducing an endothelial cell suspension into a cell growth container as described above, substantially sealing the container by heat crimping the ends, and positioning at least one retaining means, such as an o-ring washer, in close contact with the cell growth container so it remains attached. This assembly is then positioned within a rotation chamber, such as a glass or plastic test tube, and is rotated during incubation by means of a conventional rotation device well known to those skilled in the art, such as a roller drum. In this arrangement, the cell growth container is able to rotate within the rotation chamber, and multiple cell growth containers may be located within multiple rotation chambers within a single roller drum device.

The apparatus and method of the present invention provide a convenient and effective way for enhancing a sealed condition of a cell growth container, such as a synthetic graft, so as to provide a favorable environment for cell growth. The use of retaining means, such as o-ring washers, upon the external surface of the cell growth container provides an improved way for enhancing a separated relationship between the cell growth container and rotation container. This condition is favorable for enhancing temperature and humidity uniformity around and within the cell growth container.

BRIEF DESCRIPTION OF THE DRAWINGS

Other advantages of the present invention will become apparent to one skilled in the art upon reading the following specification and the following drawings.

DETAILED DESCRIPTION OF A PREFERRED EMBODIMENT

It should be understood that while this invention is described in connection with a particular example, the scope of the invention need not be so limited. Rather, those skilled in the art will appreciate that the following teachings can be used in a much wider variety of applications than the examples specifically mentioned herein.

Figure 1:
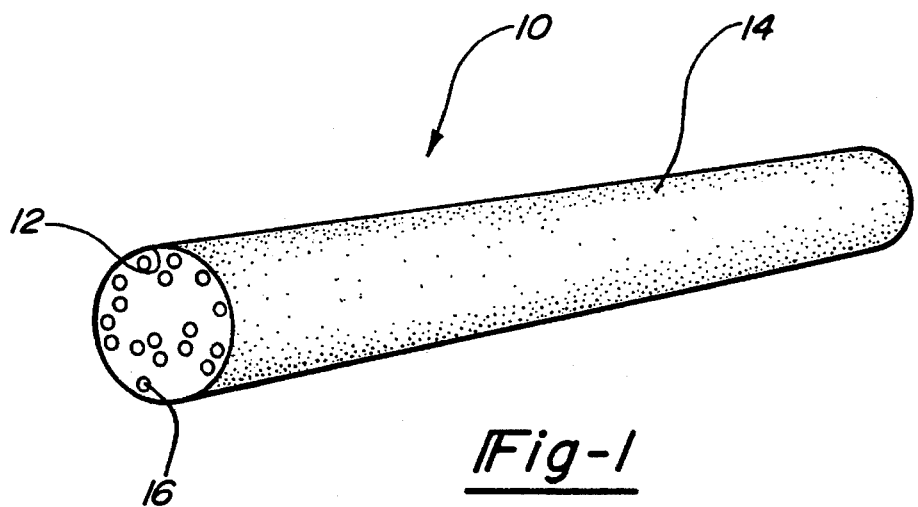
FIG. 1 is a perspective view of a prepared cell growth container in the form of a synthetic graft according to the teachings of a preferred embodiment of the present invention.

Referring now to FIG. 1, there is shown a cell growth container 10 according to the present invention. In a preferred embodiment, the cell growth container 10 is initially a hollow cylinder with open ends, having an internal growth surface 12 and an external surface 14. The cell growth container 10 is preferably made of a synthetic material capable of supporting cell growth conditions and capable of being substantially sealed by heat crimping the cylinder at each end, thereby creating a flattened mend at each end. In a preferred embodiment, the cell growth container 10 is constructed of expanded polytetrafluoroethylene (ePTFE) and is a synthetic graft of the type used as a replacement artery in a surgical procedure, where a seeding of endothelial cells on the internal surface of the graft is desired before implantation. It should be noted that in other embodiments, other suitable materials capable of supporting cell attachment and growth and capable of being heat sealed may be used, such as treated and untreated surfaces of polyacrylonitrile polymers, polystyrene, polyester and polyethylene terephthalate.

The cell growth container 10 includes on its internal growth surface 12 a cell suspension 16. The cell suspension 16 is a harvest of living cells suspended in a cell growth medium well known to those skilled in the art. Preferably, living cells are suspended in a cell growth medium, although it will be appreciated that a cell growth medium can be added to a cell suspension in other embodiments. It is the purpose of the incubation period to cause these living cells suspended in the cell growth medium to become attached to the internal growth surface 12 of the cell growth container 10 and divide, thereby forming a living cell monolayer on the internal growth surface 12.

Figure 2:
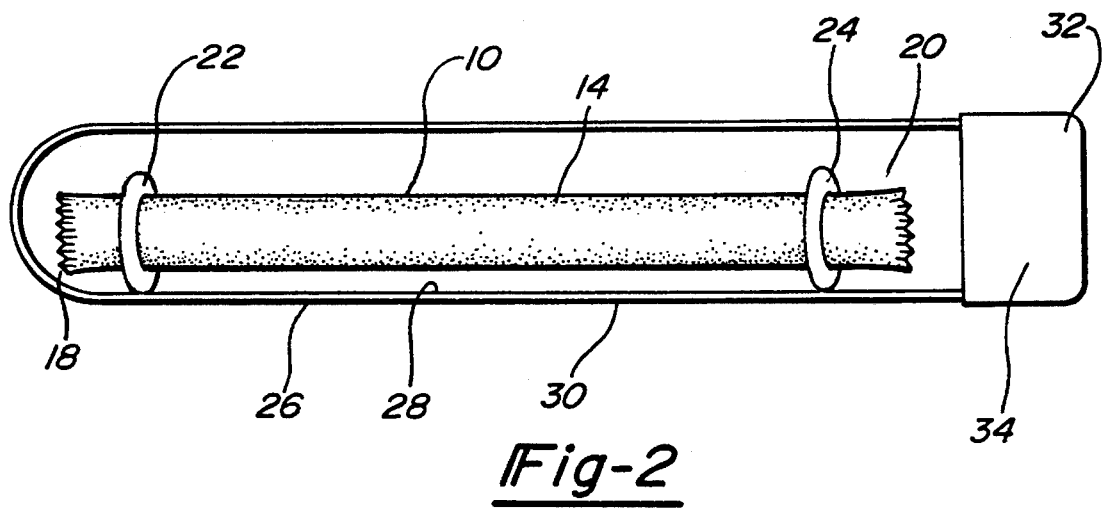
FIG. 2 is a perspective view of a prepared cell growth container heat-sealed at both ends, and disposed within a rotation container for incubation.

Referring now to FIG. 2, there is shown a cell growth container 10 in the preferred form of a hollow cylindrical synthetic graft, prepared for incubation. The cell growth container 10 includes a cell suspension (not shown) on its internal growth surface (not shown) as before. The cell growth container 10 in its prepared form is substantially sealed by heat crimped ends 18 and 20. Heat crimped ends 18 and 20 are in one preferred embodiment a pair of flattened mends created by the application of heat and localized pressure simultaneously across the diameter of the cell growth container 10 near its ends in complementary fashion from opposite directions normal to the longitudinal axis of the cell growth container 10.

The apparatus of the present invention further includes a rotation container 26 for containing the cell growth container 10 and rotating it within a rotation device of a type well known to those skilled in the art, such as a roller drum. In a preferred embodiment, the rotation container 26 is a glass or plastic test tube of a type well known to those skilled in the art, and having an internal surface 28, an external surface 30 and an open end 32, which is subsequently closed during rotation.

Alternatively, the rotation container 26 can be constructed of any other suitable material well known to those skilled in the art that will not chemically interact with or degrade the material from which the cell growth container 10 is constructed, and also will not interfere with the cell growth conditions contained therewithin. It should be noted that another suitable container besides a test tube can be employed for use as rotation container 26.

To enhance a separated relationship between the cell growth container 10 and the rotation container 26 during the incubation process, at least one retaining means is provided. In a preferred embodiment, the retaining means comprises two o-ring washers 22 and 24, positioned upon the external surface 14 of the cell growth container 10 at locations near the ends of the cell growth container 10, and in orientations substantially normal to the longitudinal axis of the cell growth container 10. O-ring washers 22 and 24 are preferably constructed to have an internal diameter substantially equal to the external diameter of the cell growth container 10, thereby enhancing a close contact between the o-ring washers 22 and 24 and the external surface 14 of the cell growth container 10. Further, o-ring washers 22 and 24 are preferably constructed to have an external diameter smaller than the internal diameter of the rotation container 26, thereby allowing a separated relation between the o-ring washers 22 and 24 and the internal surface 28 of the rotation container 26. Alternatively, the o-ring washers 22 and 24 may be constructed to have an external diameter substantially equal to the internal diameter of the rotation container 26, thereby enhancing a close contact between the o-ring washers 22 and 24 and the internal surface 28 of the rotation container 26. One or more clamp members (not shown) may also be secured to the ends of the synthetic graft 10 and secured by suitable means, such as tape, to the internal surface 28 of the rotation container 26. Both of these arrangements enhance a substantially secured relationship between the cell growth container 10 and the rotation container 26, such that the rotation of the rotation container 26 may result in a substantially synchronous rotation of the cell growth container 10.

The o-ring washers 22 and 24 are preferably constructed of a flexible material which can be easily deformed for convenience in positioning upon the external surface 14 of the cell growth container 10. It is preferred that the outer diameter of o-ring washers 22 and 24 be sized so as to allow the longitudinal insertion of the cell growth container 10 into the rotation container 26 without substantially altering the position of o-ring washers 22 and 24 upon the external surface 14 of the cell growth container 10. In addition, it is preferred that the outer diameter of o-ring washers 22 and 24 be sized so as to allow the insertion of the cell growth container 10 into the rotation container 26 to take place without the exertion of large amounts of force upon the end of the cell growth container 10. In addition, it is preferred that the o-ring washers 22 and 24 be constructed of a material that does not chemically interact with or degrade the material from which the cell growth container 10 is constructed.

The use of retaining means such as o-ring washers 22 and 24 serves to enhance temperature and humidity uniformity around and within the cell growth container 10, as well as enhancing an isolated condition from the stresses associated with a loss of frictional contact between the cell growth container 10 and the rotation container 26 during incubation. This is desirable because each loss of frictional contact between the cell growth container 10 and the rotation container 26 can be accompanied by a sudden movement of jarring sufficient to repeatedly dislodge the cells attached to the internal surface 12 of the cell growth container 10.

It should be noted that a greater or lesser number of o-ring washers may be positioned upon the cell growth container 10 for enhancing cell growth conditions of the cell growth container 10 during the rotation operation. It should also be noted that any suitable alternative retaining means can be employed for achieving the desired relationship between the cell growth container 10 and the rotation container 26.

It is essential that the rotation container 26 be enclosed with a sealing means that is complete to enhance a sealed condition within the rotation container 26, thereby inhibiting moisture or microbial transfer into or out from the rotation container 26 and thereby preventing moisture or microbial transfer to or from the cell growth container 10. In a preferred embodiment, sealing means is in the form of a cap 34 positioned in a removably secured condition against the internal surface 28 of the rotation container 26 inwardly from the open end 32. The cap 34 can be of any suitable type well known to those skilled in the art. Alternatively, sealing means can be in the form of an end clamp, heat-shrink wrap, or other closure of any suitable type well known to those skilled in the art.

In the method of the present invention, the cell growth container 10 is first prepared by introducing a cell suspension 16 into the interior of the cell growth container 10, such that it contacts the interior surface 12 of the cell growth container 10. The cell suspension 16 includes in a preferred embodiment a harvest of endothelial cells suspended in a cell growth medium. The harvesting of endothelial cells can be conducted by any method well known to those skilled in the art. For example, the prior art contains a method for harvesting endothelial cells from human umbilical veins. See Budd, J.S., et al., *Br. J. Surg.* 76:1259–1261 (1989), supra.

The method of the present invention further comprises the step of sealing each end of the cell growth container 10 by heat crimping. This procedure involves the application of heat and localized pressure simultaneously across the diameter of the cell growth container 10 near its ends in complementary fashion from opposite directions normal to the longitudinal axis of the cell growth container 10. At the same time, the circular cross section of the cell growth container 10 is squeezed to a flat configuration near each end, thereby producing substantially sealed heat crimped ends 18 and 20 near each end of the cell growth container 10. It should be noted that this procedure requires the use of a suitable material that can be heated without damage to the material and that is operable to produce a mended condition by this procedure.

The method of the present invention further comprises the step of placing retaining means such as o-ring washers 22 and 24 upon the external surface 14 of the cell growth container 10. In a preferred embodiment, this step includes the positioning of o-ring washers 22 and 24 upon the exterior surface 14 of the cell growth container 10, in orientations substantially normal to the longitudinal axis of the cell growth container 10. Once the o-ring washers 22 and 24 have been positioned upon the cell growth container 10, the cell growth container 10 and retaining means are inserted into a rotation container 26, such as the test tube described previously. It is preferred that the o-ring washers 22 and 24 remain oriented substantially normal to the longitudinal axis of the cell growth container 10, so as to provide the most effective operation of the o-ring washers 22 and 24 in enhancing a separated relationship within the rotation container 26.

The method of the present invention further includes the step of enclosing the rotation container 26 by the use of a sealing means. In a preferred embodiment, this is accomplished by inserting a cap 34 into the open end 32 of the rotation container 26 so as to become removably secured by virtue of frictional contact with the internal surface 28 of the rotation container 26. Alternatively, an end plug, heat-shrink wrap or any other closure of any suitable type well known to those skilled in the art may be employed.

Once the rotation container 26 has been substantially enclosed, the rotation container 26 containing the cell growth container 10 is placed into a rotation apparatus (not shown) of a type well known to those skilled in the art, such as a roller drum. The rotation apparatus is preferably of a type which secures the rotation container 26 by frictional contact with its external surface 30 to maintain a substantially synchronous position of the rotation container 26 and the cell growth container 10 disposed therewithin with the rotation apparatus during the rotation procedure. Thus, the rotation of the rotation apparatus preferably causes a smooth rotation of the rotation container 26 in synchronization with the rotation of the rotation apparatus, which in turn enhances a smooth rotation of the cell growth container therewithin, thereby minimizing any jarring of the cell growth container 10 which could inhibit attachment or growth of cells within the cell growth container 10.

The use of vascular grafts for the replacement of human arteries is well known in the art, and is set forth in several publications. See for example, van Oene, G.H. et al., 1st *European Workshop on Advanced Technologies in Vascular Surgery,* (1986); James, N.L., et al., *Artif. Organs* 14:355–360 (1990); Miyata, et al., *Journal of Surgical Research,* 50:485–493 (1991); Zilla, P., et al., *J. Vasc. Surg.* 6:537–541 (1987); Thomson, G.J.L., et al., *Surgery* 109:20–27 (1991); Kaehler, J. et al., *J. Vasc. Surg.* 9:535–541 (1989); Newman, K.D., et al., *J. Vasc. Surg.,* 14:140–146 (1991); Gerlach, J., et al., *Int. J. Artif. Organs* 12:270–275 (1989); and Zilla, P. et al., *Surgery* 105:515–522 (1989). All publications cited herein are incorporated by reference.

While the above description discusses a preferred embodiment of the present invention, it will be understood that the description is exemplary in nature and is not intended to limit the scope of the invention. For example, the rotation apparatus used in the present material may be of any type well known to those skilled in the art. Also, the material from which the cell growth container is made may be that which meets the criteria discussed previously, yet provides the most suitable material for the particular surgical requirement. The present invention will therefore be understood as susceptible to modification, alteration and variation by those skilled in the art without deviating from the scope and meaning of the following claims.

We claim:

1. A method for growing living cells comprising the steps of:

providing a culture including living cells and a growth medium;

introducing said culture into a hollow cylindrical cell growth container capable of being substantially sealed by heat crimping;

heat crimping said cell growth container, thereby substantially sealing said cell growth container;

positioning a fixturing means in contact with said cell growth container, thereby forming a cell growth assembly, wherein the fixturing means is a pair of o-ring members;

inserting said cell growth assembly into a rotation container, such that each o-ring is operable to enhance a separated condition of said cell growth container from said rotation container; and rotating said rotation container at a preselected rate, thereby rotating said cell growth container.

2. An apparatus for culturing living cells comprising:

a hollow cylindrical cell growth container having two ends, each end being heat crimped, said cell growth container being operable to contain a cell culture, said cell growth container being operable to be rotated by a rotation means;

a rotation container operable to contain said cell growth container: said rotation container being operable to be substantially fixedly attached in substantially synchronous relation with a rotation means; and retaining means positioned in contact with said cell growth container for enhancing a separated condition of said cell growth container within said rotation container, wherein said retaining means comprises at least one o-ring member.

3. The apparatus according to claim 2 wherein said retaining means further comprises a pair of o-ring members.

4. The apparatus according to claim 2 wherein said cell growth container comprises a synthetic graft.

5. The apparatus according to claim 4 wherein said synthetic graft comprises an expanded-polytetrafluoroethylene graft.

6. The apparatus according to claim 2 wherein said rotation container is a centrifuge tube.

7. An apparatus for culturing cells comprising:

a hollow cylindrical synthetic graft having two ends, each end being heat crimped, said synthetic graft being operable to contain a cell culture, said synthetic graft being operable to be rotated by a rotation means;

a rotation container operable to contain said synthetic graft, said rotation container being operable to be substantially fixedly attached in substantially synchronous relation with a rotation means; and a plurality of o-ring members positioned about said synthetic graft for enhancing a separated condition of said synthetic graft from said rotation container.

8. An apparatus for culturing cells comprising:

a hollow cylindrical synthetic graft having two ends, each end being heat crimped, said synthetic graft being operable to contain a cell culture, said synthetic graft being operable to be rotated by a rotation means, and wherein said synthetic graft comprises an expanded-polytetrafluoroethylene graft;

a rotation container operable to contain said synthetic graft, said rotation container being operable to be substantially fixedly attached in substantially synchronous relation with a rotation means; and a plurality of o-ring members positioned about said synthetic graft for enhancing a separated condition of said synthetic graft from said rotation container.

\* \* \* \* \*